United States Patent
Guy

(10) Patent No.: US 10,384,069 B2
(45) Date of Patent: Aug. 20, 2019

(54) TOOTH AND BONE RESTORATION VIA PLASMA DEPOSITION

(71) Applicant: Frederick R. Guy, Syracuse, NY (US)

(72) Inventor: Frederick R. Guy, Syracuse, NY (US)

(*) Notice: Subject to any disclaimer, the term of this patent is extended or adjusted under 35 U.S.C. 154(b) by 658 days.

(21) Appl. No.: 14/398,619

(22) PCT Filed: Jan. 22, 2014

(86) PCT No.: PCT/US2014/012576
§ 371 (c)(1),
(2) Date: Nov. 3, 2014

(87) PCT Pub. No.: WO2014/116722
PCT Pub. Date: Jul. 31, 2014

(65) Prior Publication Data
US 2015/0111170 A1    Apr. 23, 2015

Related U.S. Application Data

(60) Provisional application No. 61/755,092, filed on Jan. 22, 2013.

(51) Int. Cl.
*A61C 5/00* (2017.01)
*A61N 1/44* (2006.01)
(Continued)

(52) U.S. Cl.
CPC ............... *A61N 1/44* (2013.01); *A61B 17/56* (2013.01); *A61B 17/88* (2013.01); *A61B 18/042* (2013.01);
(Continued)

(58) Field of Classification Search
CPC ........... A61B 17/00; A61B 18/00; A61B 5/00; A61B 17/56; A61B 2017/564; A61C 5/062; A61C 5/04; C23C 4/04; A61N 1/44
See application file for complete search history.

(56) References Cited

U.S. PATENT DOCUMENTS 4,917,603 A * 4/1990 Haack ..................... A61C 5/12
433/29
5,128,169 A    7/1992 Saita et al.
(Continued)

FOREIGN PATENT DOCUMENTS

WO    2013014212 A2    1/2013

OTHER PUBLICATIONS

Salvatore, Claudio, "European Search Report for European Patent Application No. 14743617.4", dated Aug. 16, 2016, 7 pages.
(Continued)

*Primary Examiner* — Nicholas D Lucchesi
(74) *Attorney, Agent, or Firm* — Medley, Behrens & Lewis, LLC

(57) ABSTRACT

Aspects described herein pertain to restoring damaged portions of tooth or bone using plasma mediated deposition. In an embodiment, a biocompatible carrier gas is ionized to form a biocompatible atmospheric plasma stream. Restoration material, such as nano-scale powdered hydroxyapatite, is introduced into the plasma stream, which is then applied to a damaged portion of a bone or tooth. The restoration material is deposited on the damaged portion of the bone or tooth, thus restoring a shape and mechanical integrity of the bone or tooth.

20 Claims, 7 Drawing Sheets

(51) Int. Cl.
*A61B 17/56* (2006.01)
*A61B 17/88* (2006.01)
*A61B 18/04* (2006.01)
*A61C 5/50* (2017.01)
*A61C 5/62* (2017.01)
*A61B 18/00* (2006.01)

(52) U.S. Cl.
CPC .................. *A61C 5/50* (2017.02); *A61C 5/62* (2017.02); *A61B 2018/00291* (2013.01)

(56) References Cited

U.S. PATENT DOCUMENTS

| | | | | |
|---|---|---|---|---|
| 5,249,964 | A * | 10/1993 | Levy | A61B 18/22 433/215 |
| 5,609,921 | A | 3/1997 | Gitzhofer et al. | |
| 5,873,725 | A * | 2/1999 | Perler | A61C 13/30 433/220 |
| 6,153,266 | A | 11/2000 | Yokogawa et al. | |
| 6,214,368 | B1 | 4/2001 | Lee et al. | |
| 6,270,342 | B1 * | 8/2001 | Neuberger | A61C 1/0046 433/132 |
| 7,719,200 | B2 * | 5/2010 | Laroussi | H05H 1/2406 219/121.36 |
| 7,771,774 | B2 | 8/2010 | Berckmans, III et al. | |
| 8,192,835 | B2 | 6/2012 | Chi | |
| 8,287,914 | B2 | 10/2012 | Riman et al. | |
| 9,131,597 | B2 * | 9/2015 | Taft | A61B 18/148 |
| 9,204,950 | B2 * | 12/2015 | Liu | A61C 19/00 |
| 9,393,217 | B2 * | 7/2016 | Hammond | A61K 9/7007 |
| 2002/0102520 | A1 | 8/2002 | Iiyama et al. | |
| 2003/0199866 | A1 * | 10/2003 | Stern | A45D 44/22 606/41 |
| 2003/0219390 | A1 | 11/2003 | Santarpia, III et al. | |
| 2004/0202985 | A1 * | 10/2004 | Karmaker | A61C 5/04 433/220 |
| 2004/0241613 | A1 | 12/2004 | Jansen et al. | |
| 2005/0153069 | A1 | 7/2005 | Tapphorn et al. | |
| 2006/0136068 | A1 * | 6/2006 | de Bruijn | A61L 27/12 623/23.63 |
| 2006/0251795 | A1 * | 11/2006 | Kobrin | A61L 27/34 427/2.1 |
| 2007/0029500 | A1 * | 2/2007 | Coulombe | H01T 23/00 250/423 F |
| 2007/0160958 | A1 * | 7/2007 | Belikov | A61C 19/063 433/215 |
| 2007/0173950 | A1 * | 7/2007 | Zanella | A61L 27/50 623/23.63 |
| 2007/0259427 | A1 * | 11/2007 | Storey | A61F 2/30767 435/402 |
| 2008/0149566 | A1 | 6/2008 | Messersmith et al. | |
| 2008/0280260 | A1 | 11/2008 | Belikov et al. | |
| 2009/0142514 | A1 * | 6/2009 | O'Neill | H05H 1/46 427/595 |
| 2009/0270527 | A1 * | 10/2009 | Lin | A61K 6/08 523/116 |
| 2010/0047733 | A1 * | 2/2010 | Nahlieli | A61B 1/018 433/29 |
| 2010/0273129 | A1 * | 10/2010 | Yu | A61C 5/00 433/217.1 |
| 2010/0324564 | A1 * | 12/2010 | Bjursten | A61B 17/7095 606/92 |
| 2011/0125156 | A1 * | 5/2011 | Sharkey | A61B 17/1764 606/92 |
| 2011/0159273 | A1 * | 6/2011 | Lukowski | A61K 9/5123 428/323 |
| 2012/0052183 | A1 * | 3/2012 | Wu | A61L 27/32 427/2.1 |
| 2012/0095558 | A1 * | 4/2012 | Wooley | A61F 2/28 623/16.11 |
| 2012/0141775 | A1 * | 6/2012 | Ahmed | B22F 1/02 428/323 |
| 2012/0259272 | A1 | 10/2012 | Staack et al. | |
| 2012/0276336 | A1 | 11/2012 | Malshe et al. | |
| 2013/0035561 | A1 * | 2/2013 | Sharkey | A61B 5/4528 600/301 |
| 2013/0059273 | A1 | 3/2013 | Koo et al. | |
| 2013/0253661 | A1 * | 9/2013 | D'Agostino | A61K 9/0024 623/23.51 |
| 2014/0170410 | A1 * | 6/2014 | Rupprecht | C23C 4/00 428/327 |
| 2014/0171854 | A1 * | 6/2014 | Jacofsky | A61M 37/00 604/23 |
| 2016/0106838 | A1 * | 4/2016 | D'Agostino | A61B 17/7233 623/23.51 |
| 2016/0256607 | A1 * | 9/2016 | Francis | A61L 27/3608 |
| 2018/0223260 | A1 * | 8/2018 | Aprikyan | C12N 5/0696 |

OTHER PUBLICATIONS

Aparicio, et al., "Variation of Roughness and Adhesion Strength of Deposited Apatite Layers on Titanium Dental Implants", Materials Science and Engineering, vol. C, No. 31, 2011, pp. 320-324.

Ryu, et al., "Mussel-Inspired Polydopamine Coating as a Universal Route to Hydroxyapatite Crystallization", In Advanced Functional Materials, vol. 20, 2010, pp. 2132-2139.

Kumar CH, et al., "Plasma Torch Toothbrush a New Insight in Fear Free Dentistry", Jun. 20, 2014, 4 pages.

Ameen, Mohammad M., "Non-Final Office Action for U.S. Appl. No. 15/868,115", dated May 18, 2018, 14 pages.

European Patent Office, "Communication Under Rule 71(3) EPC for European Patent Application No. 14743617.4", dated Jan. 9, 2018, 30 pages.

* cited by examiner tion site. (B) Depositing the restoration material on an application site; and directing a plasma stream onto the restoration material on the application site. In either case, the application site is a damaged area of a tooth or bone.

A method of repairing teeth or bone, the method includes: affixing biocompatible nano-scale hydroxyapatite onto a damaged portion of a bone or tooth, wherein the hydroxyapatite is adhered via plasma mediated deposition using biocompatible gases, and wherein the plasma mediated deposition is conducted at a biocompatible temperature; and restoring a shape and a mechanical integrity of the damaged portion of the bone or tooth with the hydroxyapatite.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

TOOTH AND BONE RESTORATION VIA PLASMA DEPOSITION

BACKGROUND

The present disclosure relates generally to tooth and bone restoration. More specifically, the present disclosure relates to restoring damaged portions of teeth or bone using plasma mediated deposition.

Plasma techniques such as physical vapor deposition or plasma-enhanced chemical vapor deposition are known. Plasma-related techniques have been used in dentistry for sterilization and surface preparation to enhance adhesive properties of dental materials, but have not been used to restore damaged portions of teeth or bone. Other procedures that can halt advancing tooth decay or promote bone recovery, such as periodontal surgery, bone grafts, prosthesis implants, are often difficult, invasive and expensive to implement, and have limited, if any, success in actually restoring bone or enamel.

SUMMARY

The following is a brief summary of subject matter that is described in greater detail herein. This summary is not intended to be limiting as to the scope of the claims.

A non-thermal plasma deposition device, includes an ionization chamber configured to: receive a carrier gas and excite the carrier gas to form an ionizing plasma stream. The ionization chamber further comprises an inlet coupled to a restoration material supply, the inlet intersects with the ionization chamber in a location after the ionizing plasma stream is formed. The ionization chamber is further configured to receive the restoration material and introduce the restoration material into the ionizing plasma stream to form a deposition stream. The deposition nozzle is configured to eject a plume of the deposition stream to deposit the restoration material on an application site. The restoration material is thus deposited on and adhered to the application site via plasma mediated deposition. A shape and mechanical integrity of a damaged portion of a tooth or bone can thus be restored.

In some embodiments, the restoration material is hydroxylapatite ("HAP"), or a derivative thereof. HAP or derivatives thereof are primary constituents of organic bone material. Nano-scale powdered HAP, when deposited via plasma mediated deposition, crystallizes and forms a structure that comports with a crystalline structure of the tooth or bone of the application site.

In some embodiments, a camera disposed proximate to the plume and directed towards the application site is used to capture images of the deposition of restoration material. Not only can such images be recorded for use during diagnosis and comparison, etc., but also such images can be used to provide vision of the deposition when such view may otherwise be obstructed. In some embodiments, an exhaust hood is used to encapsulate the plume and application site. The exhaust structure may be coupled to a vacuum. Surrounding biological material can thus be protected. Residue of the deposition may also be vacated or vacuumed, etc., via an exhaust outlet in the exhaust hood.

A method for repairing a damaged bone or tooth includes exciting a carrier gas to form an atmospheric plasma stream; and either (A) or (B). (A) introducing a restoration material into the plasma stream to form a deposition stream; and depositing the restoration material on an application site by ejecting a plume of the deposition stream to the application site. (B) Depositing the restoration material on an application site; and directing a plasma stream onto the restoration material on the application site. In either case, the application site is a damaged area of a tooth or bone.

DETAILED DESCRIPTION

Figure 1:
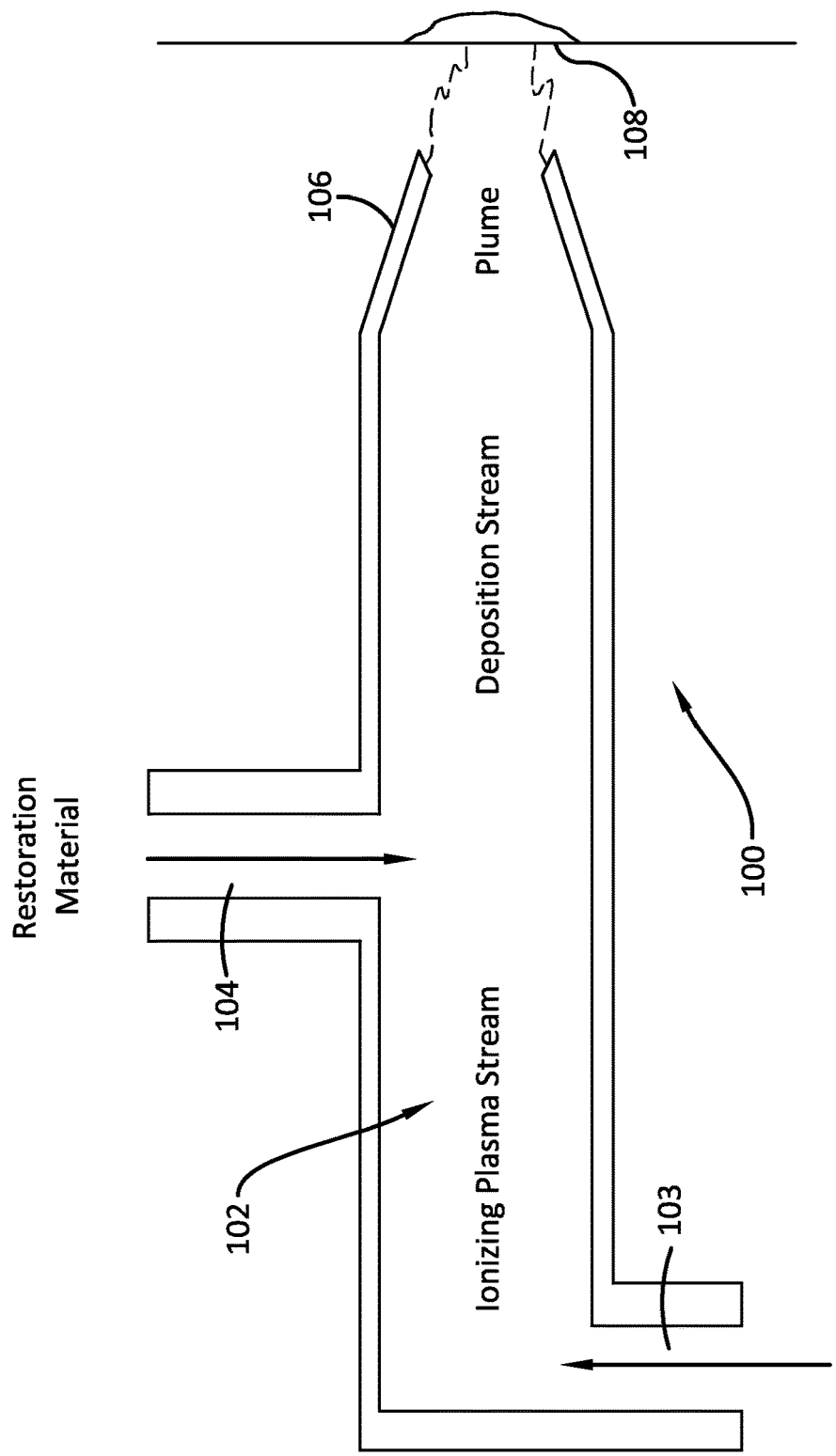
FIG. 1 is a cross-sectional view of an exemplary non-thermal plasma deposition device.

Various technologies pertaining to restoring damaged portions of tooth or bone using plasma mediated deposition are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, structures and devices are shown in block diagram form in order to facilitate describing one or more aspects. Further, it is to be understood that functionality that is described as being carried out by certain components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. Additionally, as used herein, the term "exemplary" is intended to mean serving as an illustration or example of something, and is not intended to indicate a preference. The articles "a," "an," and "the" should be interpreted to mean "one or more" unless the context clearly indicates the contrary. The term "includes" is used interchangeably with the term "comprising."

Aspects described herein pertain to restoring damaged portions of tooth or bone using plasma mediated deposition. In a general embodiment, a biocompatible carrier gas is ionized to form a biocompatible atmospheric plasma. Restoration material is introduced into the plasma, which is then applied to a damaged portion of a bone or tooth. The restoration material is deposited on and is permanently affixed to the damaged portion of the bone or tooth, thus restoring a shape and mechanical integrity of the bone or tooth.

With reference now to FIG. 1, an exemplary embodiment of a non-thermal plasma ("NTP") deposition device 100 that facilitates restoration of tooth or bone is illustrated. The term "plasma" refers to a partially or wholly ionized gas composed essentially of photons, ions and free electrons as well as atoms in their fundamental or excited states possessing a net neutral charge. Plasma possesses a net neutral charge because the number of positive charge carriers is equal to the number of negative ones. An NTP refers to a plasma that is near ambient temperature (e.g., from 20° C. to 60° C., or 25° C. to 40° C., or 22° C. to 30° C.) that is obtained at atmospheric or reduced pressures. For example, remote treatment, direct treatment, or electrode contact NTP may be used, also, afterglow or active plasma methods may be used. In one embodiment at least a partial vacuum is applied to enhance the process. In an embodiment, the plasma deposition process does not include sputtering processes. In an embodiment of the device and process described herein plasma polymerization occurs where the restoration material is a polymerizable material (or monomer) that is introduced into the plasma stream.

As shown in FIG. 1, the NTP deposition device 100 comprises an ionization chamber 102 that is configured to receive a carrier gas and excite the carrier gas to form an ionizing plasma stream. The ionization chamber 102 further comprises carrier gas inlet 103, and a restoration material inlet 104 that is configured to receive a restoration material, such as a bone or tooth restoration material, and introduce the restoration material into the ionizing plasma stream to form a deposition stream. The inlet 104 is coupled to the ionization chamber 102 and is disposed along a length of the ionization chamber 102. The interior of the inlet 104 intersects with the interior of the ionization chamber 102 in a location between the ionizing plasma stream and a deposition nozzle 106. The intersection is after the ionizing plasma stream has been activated. In an embodiment utilizing internal electrodes the inlet 104 is placed away from the electrode gap, such as at least 0.25 mm, at least 1 mm, or at least 5 mm from the electrode gap. A deposition nozzle 106 is configured to receive the deposition stream, and shape a plume of the deposition stream to conform to a desired application site 108. The deposition nozzle 106 directs the deposition stream onto the application site 108 and deposits the restoration material onto the application site 108 via plasma mediated deposition of the plume of the deposition stream.

In an embodiment, the NTP deposition device 100 is dimensioned to be handheld and light enough for easy manipulation in small work areas such as a patient's mouth or a surgical incision. Form-factors similar to an endoscope or a wand used in 3-D imaging for dentistry may be utilized.

The carrier gas is a biocompatible gas that is not harmful to tooth, bone, or surrounding biological tissue. The carrier gas can comprise, for example, helium, oxygen, nitrogen, argon, ambient air, or combinations thereof. In an embodiment, the carrier gas is a non-reactive gas. Carrier gas is introduced into the ionization chamber 102 from a supply such as a pressure vessel or supply feed. A flow rate of the carrier gas into the ionization chamber 102 can be controlled by, for example a valve. For example, the flow rate of the carrier gas into the ionization chamber can be restricted to 5 mL per minute to 15 L per minute, such as 500 mL per minute to 10 L per minute, or 1 L per minute to 5 L per minute. A desired flow rate for the carrier gas may depend on desired characteristics of the ionizing plasma stream as well as characteristics of the ionization chamber 102.

The ionization chamber 102 excites the carrier gas to form the ionizing plasma stream. For example, subjecting the carrier gas to high energy ultraviolet light, (e.g., radiation having a wavelength between 180 nm to 270 nm), microwaves (e.g., radiation having a frequency of 2.4 GHz or more), or an electric discharge with a high voltage difference can result in the formation of an ionizing plasma. In an example, the ionization chamber 102 comprises a pair of electrodes, or an electrode and a grounded connection, which creates a voltage difference across the carrier gas within the ionization chamber 102. A current source, such as a 10 kHz, 20 kHz, or 40 kHz, or alternating current, can be used to drive the voltage difference. The voltage difference needed to excite the carrier gas may depend on the carrier gas selected, a shape of discharge needle, and an impedance matching network of the NTP deposition device 100, and other factors.

In an embodiment the plasma source is a capacitively coupled radio frequency (13.56) MHz discharge created the tip of a sharp needle.

While electron temperature may be very high, due to the excitation, the macroscopic temperature of the ionizing plasma stream remains close to room temperature. This is because of low power consumption (e.g., 100 mW), convective cooling, and/or a small volume size of plasma ejected by the NTP deposition device 100. The plasma ejected from the NTP deposition device 100, the "plume," has a small volume, (e.g., 0.01 mm$^3$ to 2 mm$^3$, 0.1 mm$^3$ to 1 mm$^3$, or 0.5 mm$^3$ to 1.5 mm$^3$) and a relatively large surface to volume ratio, which promotes energy escape by thermal diffusion.

The inlet 104 in the ionization chamber 102 is also in communication with a feed of restoration material. In an embodiment, the inlet 104 is coupled to a container with a supply of restoration material that may be pressurized, for example, the restoration material may be pumped, pushed, or gravity fed into the inlet 104. In an example, the restoration material is aerosolized with a gas such as a carrier gas before being fed into the inlet 104.

The restoration material is a material that, when deposited on and affixed to tooth enamel, dentin, or bone, crystalizes and adheres to crystalline elements of the tooth enamel, dentin, or bone. By depositing the restoration material on a damaged portion of enamel, dentin, or bone, the damaged portion may thus be restored. In an embodiment, the restoration material is a nano-scale powder suitable for being introduced into the ionizing plasma stream. The restoration material can comprise a variety of materials such as HAP, nano-scale diamonds, calcium apatite, or other minerals or materials. In an embodiment, the restoration material is exclusive of zircon-oxide, poly(methyl methacrylate), polyethylene, metal, or glass.

Calcium apatite, $Ca_5(PO_4)_4(R)$, where R is an end-member, is a mineral produced and used by biological microenvironment systems. Species of calcium apatite include hydroxylapatite, $Ca_5(PO_4)_4(OH)$ ("HAP"), flourapatite, $Ca_5(PO_4)_4(F)$, and chlorapatite, $Ca_5(PO_4)_4(Cl)$. Portions of bone material comprise HAP wherein many of the OH groups are missing and contain many carbonate and acid phosphate substitutions. In an example, the restoration material is a nano-scale powder of HAP, carbonated calcium-deficient HAP with acid phosphate substitutions, or derivatives or substitutions thereof. In an embodiment, the manufactured nano-scale powders are dimensioned to approximately match a size of naturally occurring tooth enamel and bone crystals, for example 500 nm to 40 micrometers, such as 1 micrometer to 20 micrometers, or 2 micrometers to 10 micrometers. Thus, when deposited via plasma mediated deposition, the size of the nano-scale powder may promote crystallization of the restoration material that conforms with a crystalline structure of tooth enamel or bone. The restoration material should have ionic bonding qualities needed to achieve a non-toxic, biocompatible, permanent reconstruction of tooth and/or bone. It was also surprisingly found that the NTP deposition process causes additional crystallization in the restoration material.

Introducing the restoration material via the inlet 104 into the ionizing plasma stream in the ionization chamber 102 forms a deposition stream. The deposition nozzle 106 receives the deposition stream, and shapes the plume of the deposition stream to conform to a desired application site 108. The plume is ejected proximate to the application site, thus depositing bone restoration material on the application site. A distance between the deposition nozzle 106 and the application site is selected such that bone restoration material adheres to, but does not damage the application site. Such distance may be calibrated based on, for example, a flow rate of the carrier gas, a flow rate of the restoration material, a size of the application site, and/or other factors. Example distances from the nozzle tip to the application site 108, include 0.001 mm to 5 mm, 0.01 mm to 3 mm, or 0.1 mm to 1.5 mm.

While the deposition stream is at a temperature that is not harmful to biological material, it may be desirable to deposit restoration material on the application site 108 exclusive of any surrounding biological material. Thus, in an embodiment the deposition nozzle 106 is configured to adjust a size and shape of the plume of the deposition stream.

In an embodiment, the inlet 104 may be external and intersect with the plasma stream after it passes through the deposition nozzle 106.

A desired application site 108 may be, for example, a dental cavity, a bone fracture, a bone spur, a weakened or damaged portion of a tooth or bone, a degenerated disk, an arthritic joint, a void (or chip) in a tooth or bone, a groove in a teeth, such as may be caused by severe bruxism, or a combination thereof.

For treatment of bone damage, surgical techniques such as arthroscopic surgery may be adapted for use with the device 100.

Figure 2:
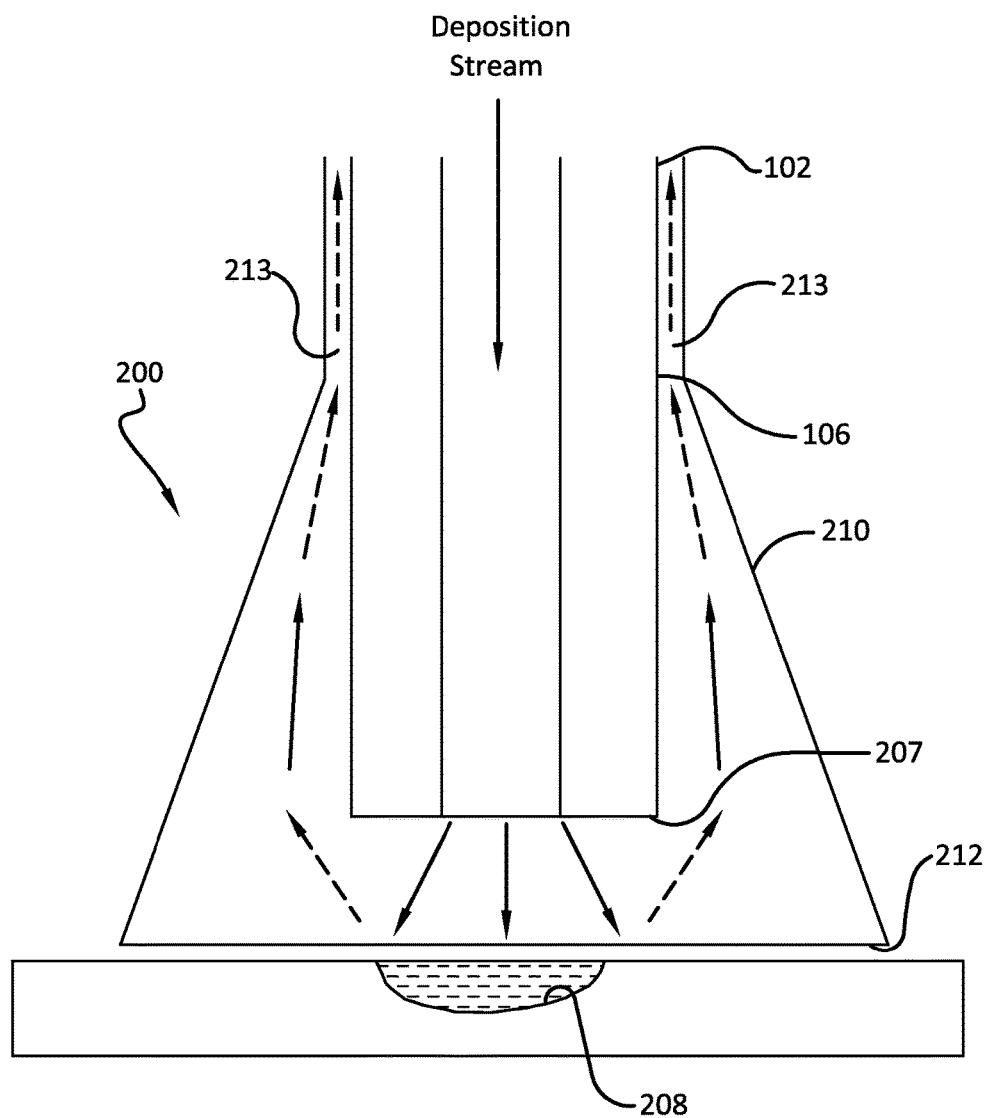
FIGS. 2 and 3 are flow diagrams of exemplary methodologies that facilitate restoring tooth or bone via plasma mediated deposition of restoration material.

In an embodiment depicted in FIG. 2, an NTP deposition device 200 further comprises an exhaust hood 210 configured to vacate residue of the deposition stream from the application site 208 (which in this case is depicted as a cavity on a tooth surface) and/or provide at least a partial vacuum in the volume that is encompassed by the exhaust hood 210 and near the application site 208. Depending on the strength of the vacuum, the volume under vacuum may extend from a terminal circumferential edge 212 of the exhaust hood 210 from 0.001 mm, to 5 mm, such as 0.01 mm to 2 mm, or 0.1 mm to 1 mm.

In an example, the exhaust hood 210 uses suction or a vacuum to extract the residue. The exhaust hood 210 may be a cup, hood, skirt, funnel or another structure configured to encapsulate the deposition nozzle 106 and cover over the application site 208 so as to capture restoration material that does not adhere to bone or tooth and/or the ionized gasses in the deposition stream. The exhaust hood 210 may comprise a rigid or flexible material. For example, the material may be a soft elastomeric material, a hard plastic material, a rigid metal material, or a soft, but stiff elastomer that will hold its form under vacuum, but will conform to the application site 208 if pushed against it.

In an embodiment, the exhaust hood 210 is co-axial with and coupled to the ionization chamber 106 or deposition nozzle 206 and circumscribing an area centered about the deposition nozzle 106. A terminal circumferential edge 212 of the exhaust hood 210 may extend 0.1 mm to 5 mm in radius about the deposition nozzle 106, such as 0.5 mm to 2 mm, or 1 mm to 1.5 mm. The terminal circumferential edge 212 may extend to be coplanar with a terminal end of the deposition nozzle 207, or extend within 10 mm past a plane with the terminal end of the deposition nozzle 207, such as 0.5 mm to 5 mm, or 1 mm to 1.5 mm.

The terminal circumferential edge 212 of the exhaust hood 210 can be placed against the application site 208 so that the deposition nozzle 106 and the plume are substantially or completely encapsulated. In an embodiment, the circumferential edge 212 of the exhaust hood 210 is from 0.001 mm to 5 mm in proximity to the application site 208, such as 0.01 mm to 2 mm, or 0.1 mm to 1 mm. In an embodiment, the circumferential edge 212 rests against the surrounding tissue or area around the application site 208.

In an embodiment, the exhaust hood 210 is moveable in an axial direction along the outer surface of the ionizing chamber 102 and deposition nozzle 106. For example, the exhaust hood 210 may be coupled to the ionizing chamber 102 through a sliding mechanism or a sliding and locking mechanism. In FIG. 2, the exhaust hood 210 is concentrically fitted slideably coupled around the ionization chamber 102 and nozzle 106.

In an embodiment, a tightened screw locking mechanism, such as a thumb screw, may be coupled to the exhaust hood 210 and may be tightened against the ionization chamber 102 and untightened to lock and unlock the slideable coupling. In another embodiment, the locking mechanism may be a tooth-in-groove structure or a reciprocating ratcheting mechanism. In an embodiment the exhaust hood 210 can be coupled to the ionizing chamber 102 through a tight fitting cap or ring that is slideable along the outer surface of the ionizing chamber 102. In an embodiment, the exhaust hood 210 is also configured to be locked into an axial position to prevent unwanted movement. This may be accomplished by known locking mechanisms for axially moveable parts, such as an insertable pin or lever that arrests movement in the axial direction. Axial rotation may also be prevented by known mechanisms including levers, pins, or detents.

The vacuum exhaust outlet 213 is shown as extending up along the side of the ionization chamber 102. The exhaust outlet may circumscribe the entire lower portion of the ionization chamber 102 or only partially circumscribe a portion of it. In other embodiments, the exhaust outlet 213 is coupled to the exhaust hood 210 near the circumferential edge 212 of the exhaust hood 210, such as 0.01 mm to 3 mm, 0.1 mm to 2 mm, or 0.5 mm to 1.5 mm from the circumferential edge 212 of the exhaust hood 210.

The exhaust outlet 213 is in communication with a vacuum device, such as an electric powered vacuum mechanism, or other known vacuum device. In an embodiment, the vacuum suction power (or pressure) is adjustable to levels desired to produce a vacuum that removes loose material and/or reduces heat build-up in the affected area. In an embodiment, the vacuum power is limited to a pressure that is less than a power that would disrupt the restoration material that is deposited onto the application site 208. In an embodiment, the vacuum power is high enough to affect the plasma deposition process, as certain plasma deposition processes may be enhanced in a vacuum environment. In an embodiment, the vacuum power is enough to remove debris, but has no effect on the deposition process. In an embodiment, the vacuum provides a drop from 99% to 1% of atmospheric pressure, e.g. (1 atm), such as 95% to 50%, or 90% to 75% of atmospheric pressure.

The exhaust hood 210 may be adjustable so that the diameter of at least portions of the exhaust hood 210, including the terminal circumferential edge 212, can be increased or decreased. This may be accomplished by using a structure similar to a camera aperture. Where multiple overlapping curvilinear panels are utilized to form the hood structure. In an embodiment, the exhaust hood 210 may be removable and replaceable with exhaust hoods of various shapes and features to adapt device 200 to the shape and conditions of the affected tooth, bone, or surrounding area. For example, the edge of a tooth, such as a bicuspid, may benefit from having an extended piece that wraps around the side of the tooth and where the vacuum exhaust outlet 213 is below the level of the application site 208 or to the side of the application site 208.

In an alternate embodiment, a structure similar to the exhaust hood 210, such as a protective hood, is coupled to the NTP deposition device 200, but does not include any exhaust outlet 213 or vacuum mechanism. In this embodiment the protective hood operates to merely protect surrounding tissue from deflected deposition material and heat. This option may be useful for operating on an application site that is locally numbed, if proper care is taken. The protective hood may also be combined with the camera and adjustability features described herein.

Figure 3:
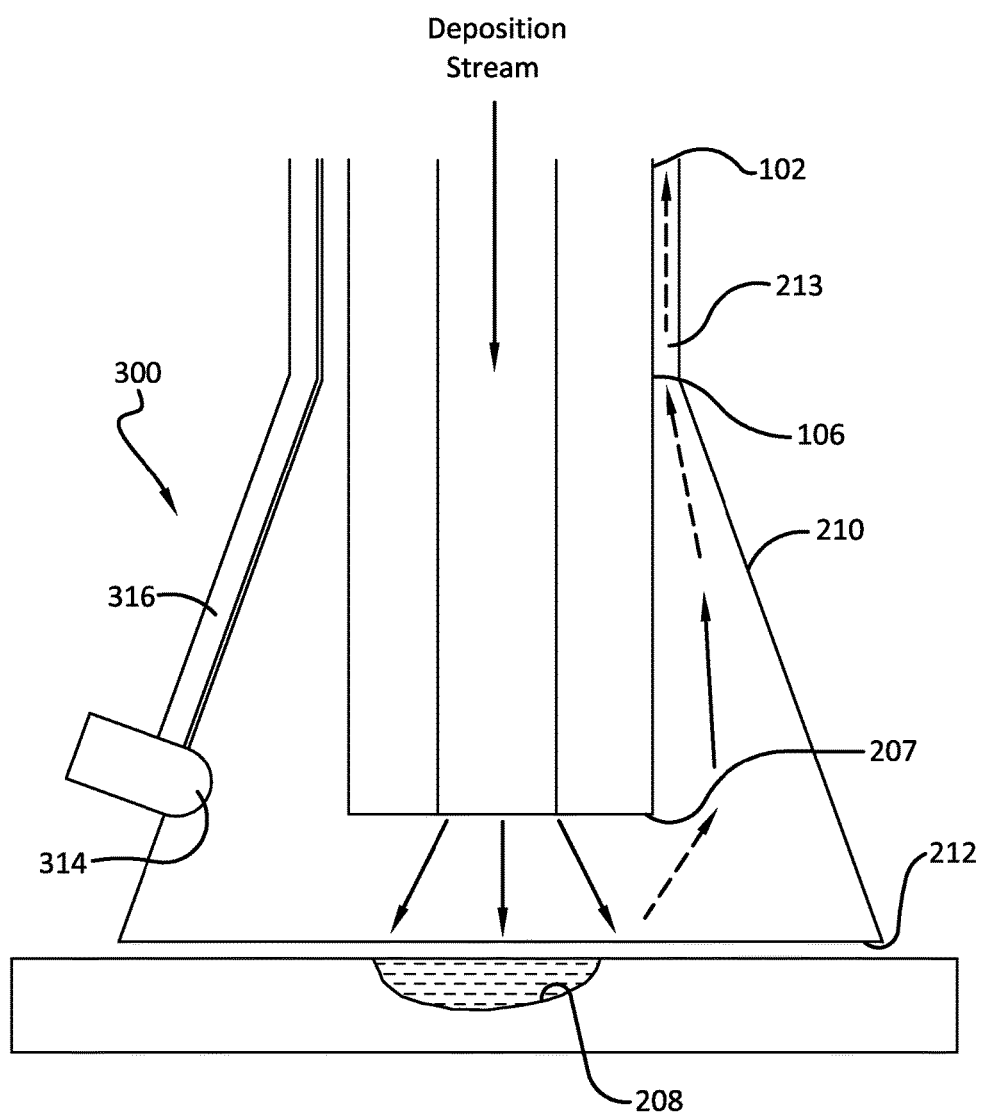

In another embodiment, shown in FIG. 3, an NTP deposition device 300 can further comprise a camera 314 configured to capture images of the deposition of the restoration material on the application site 308 (in this example a bone surface with a chip or fracture). The camera 314 may capture still or moving images of the deposition of the restoration material. Captured images may be used to show a before/after change resulting from the deposition, or may be used in diagnosis or patient evaluation. Additionally, captured images can be used to provide the operator of the NTP deposition device 300, such as a dentist, orthodontist, or surgeon with additional vision during the deposition process. In an example, a portion of the application site 308 may be obstructed from view of an individual using the NTP deposition device 300 by teeth, bone, other biological material, or the exhaust hood 210. An obstructed view can inhibit the accuracy, efficiency, and precision of the deposition, and can lead to waste of materials such as carrier gas and/or restoration deposition material.

Images captured from the camera 314 disposed on the NTP deposition device 300 can, for example, be transmitted to and displayed on a video display visible by the operator using the NTP deposition device.

In an embodiment, at least a portion of the camera 314 is disposed within the exhaust hood 210. As the exhaust hood 210 may obstruct the application site 308, disposing the camera 314 within the exhaust hood 210 enables vision of the application site 308 while protecting surrounding biological material and evacuating residue of the deposition. Wiring or optical cables 316 for the camera 314 may run closely along the exterior of the device 300.

In an embodiment, the camera 314 may be disposed opposite an exhaust outlet 213 within the exhaust hood 210 so as to reduce an amount of residue build-up on the camera 314.

Figure 4:
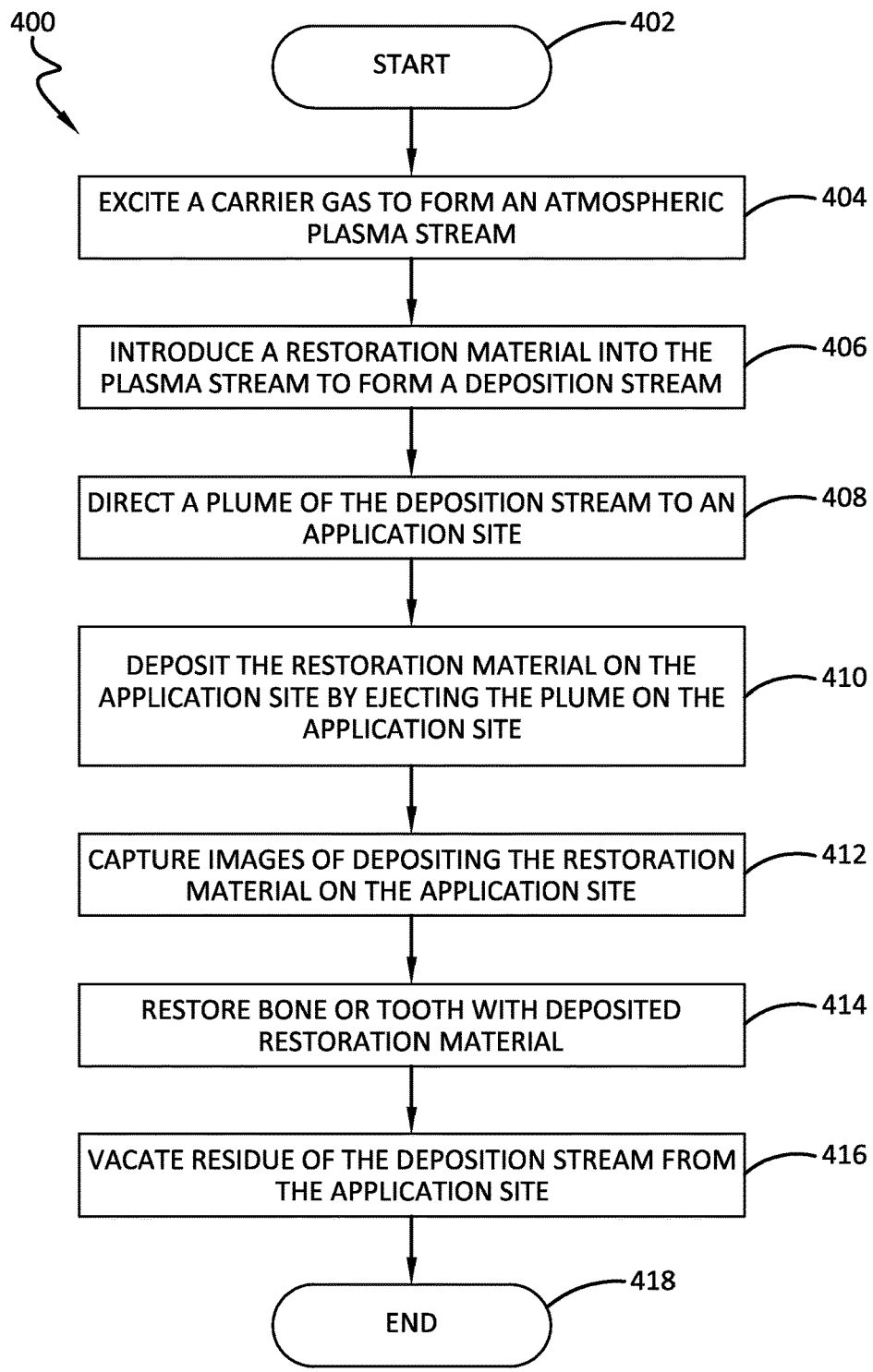
FIG. 4 is a cross-sectional view of an embodiment of the plasma deposition device with an exhaust structure.
Figure 5:
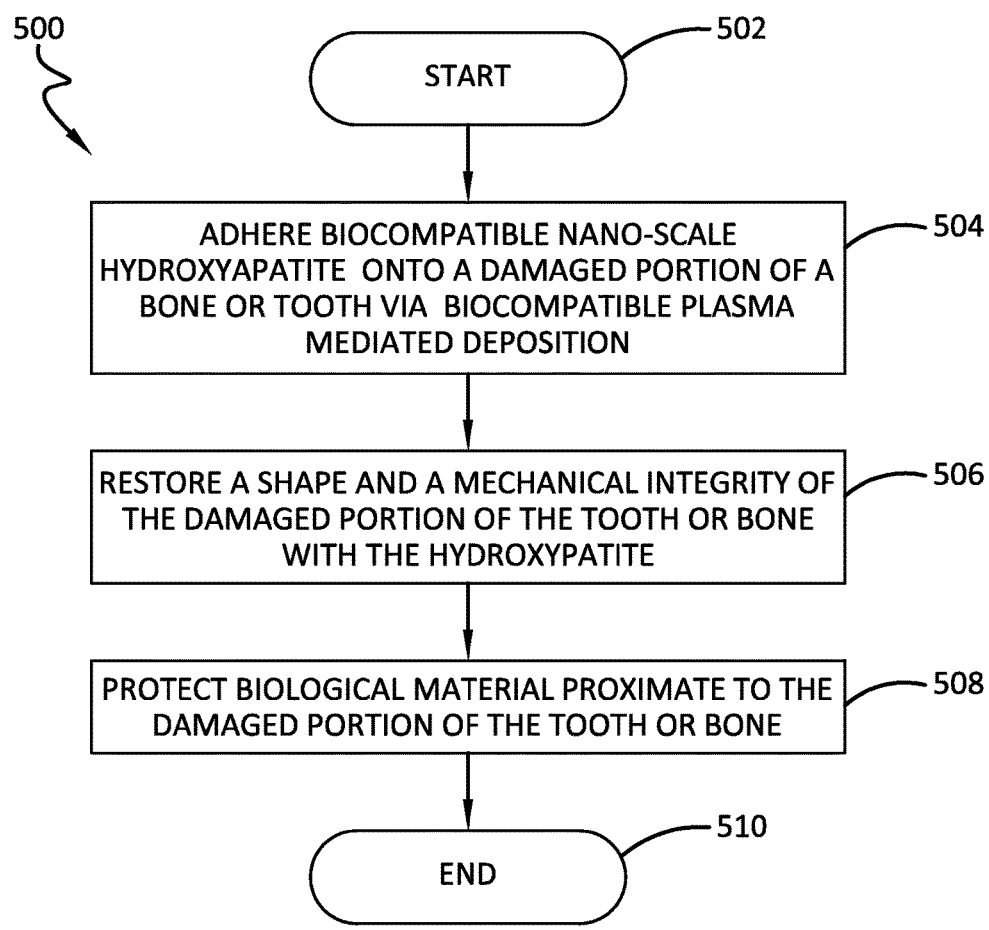
FIG. 5 is a cross-sectional view of an embodiment of the plasma deposition device with a camera and an exhaust structure.

With reference now to FIGS. 4 and 5, various exemplary methodologies are illustrated and described. While the methodologies are described as being a series of acts that are performed in a sequence, it is to be understood that the methodologies are not limited by the order of the sequence. For instance, some acts may occur in a different order than what is described herein. In addition, an act may occur concurrently with another act. Furthermore, in some instances, not all acts may be required to implement a methodology described herein.

Referring now to FIG. 4, an exemplary methodology 400 that facilitates restoring bone, enamel, or combinations thereof via atmospheric plasma mediated deposition is illustrated. The methodology 400 starts at 402, and at 404 a carrier gas is excited to form an atmospheric plasma stream. The carrier gas is a biocompatible, non-toxic gas, and can be excited via various techniques such as, for example, being exposed to a voltage difference across an ionization chamber. At 406, a restoration material is introduced into the plasma stream to form a deposition stream. The restoration material is as described above, a material that, when deposited on tooth or bone, crystallizes with a structure that comports with a crystalline structure of the tooth or bone. In an example, the restoration material is a nano-scale powder of hydroxyapatite. The restoration material may be introduced into the plasma stream via a variety of techniques such as, for example, spraying, aerosolizing, or mixing.

At 408, a plume of the deposition stream is directed to a desired application site. In an example, a nozzle shapes the plume to a size suitable for a particular application site such that surrounding biological material is protected from the deposition stream. At 410, restoration material is deposited on the application site by ejecting the plume proximate to the application site.

Optionally, at 412, images of depositing restoration material on the application site are captured. Such images may be captured, for example, by a camera directed towards the application site and disposed proximate to the plume.

At 414, bone or tooth damage at the application site are restored with the deposited restoration material. Restoration of the application site may include filling a void, such as a fracture, indentation, or crack back to its original state. For example, this may include filling the void up to a plane running across the highest edges of an indentation, fracture, or crack and possibly slightly exceeding the plane to substantially restore the original shape. For example, a crack may be filled within 10%, such as within 5%, or 2% of its volume or its distance over or beneath the plane.

In an embodiment, the restoration is not a mere thin coating on the surface of the application site, nor is it an adhesive by which additional material is added. Rather, the restoration deposition has a substantial thickness and fills up a voided area that has suffered the loss of original material that has abraded, broken, or otherwise decayed away. In an embodiment, the restoration deposition has a thickness of 0.001 mm to 35 mm, 0.1 mm to 5 mm, or 10 mm to 25 mm.

Optionally, at 416, residue of the deposition stream is vacated from the application site. The residue may be vacated by, for example, an exhaust hood, or vacuum, etc., disposed proximate to the plume. Residue may include, for example, excess restoration material, heat, and/or carrier gas. The methodology ends at 418.

Referring now to FIG. 5, an exemplary methodology 500 that facilitates restoring a shape and mechanical integrity of a damaged portion of tooth or bone with hydroxyapatite is illustrated. The methodology 500 starts at 502, and at 504, biocompatible nano-scale hydroxyapatite is adhered onto a damaged portion of a bone or tooth via biocompatible plasma mediated deposition. At 506, a shape and mechanical integrity of the damaged portion of tooth or bone is restored with the hydroxyapatite. At 508, biological material proximate to the damaged portion of tooth or bone is protected from the plasma mediated deposition. The methodology ends at 510.

In an embodiment of this method 500, the restoration material is introduced after the deposition nozzle. For example, the restoration material may be deposited via a solution onto the application site and then ionized by the plasma gases that have no deposition material directly in the stream.

In an embodiment, a system or kit comprises a non-thermal plasma deposition device as disclosed herein. The system or kit also comprises one or more of the following: a restoration material, a supply container for the restoration material, a biocompatible carrier gas supply, a biocompatible carrier gas, an exhaust hood, a protective hood, a camera for capturing images of the restoration material deposition, a display for displaying the camera images, a vacuum device, a pressurization device, and conduits or wiring for connecting any of the components listed herein. The kit or system may be utilized to operate the methods for tooth or bone restoration disclosed herein.

EXAMPLES

In Examples 1 and 2 deposition of hydroxylapatite with a non-thermal plasma deposition technique and device was demonstrated.

Example 1

Figure 6:
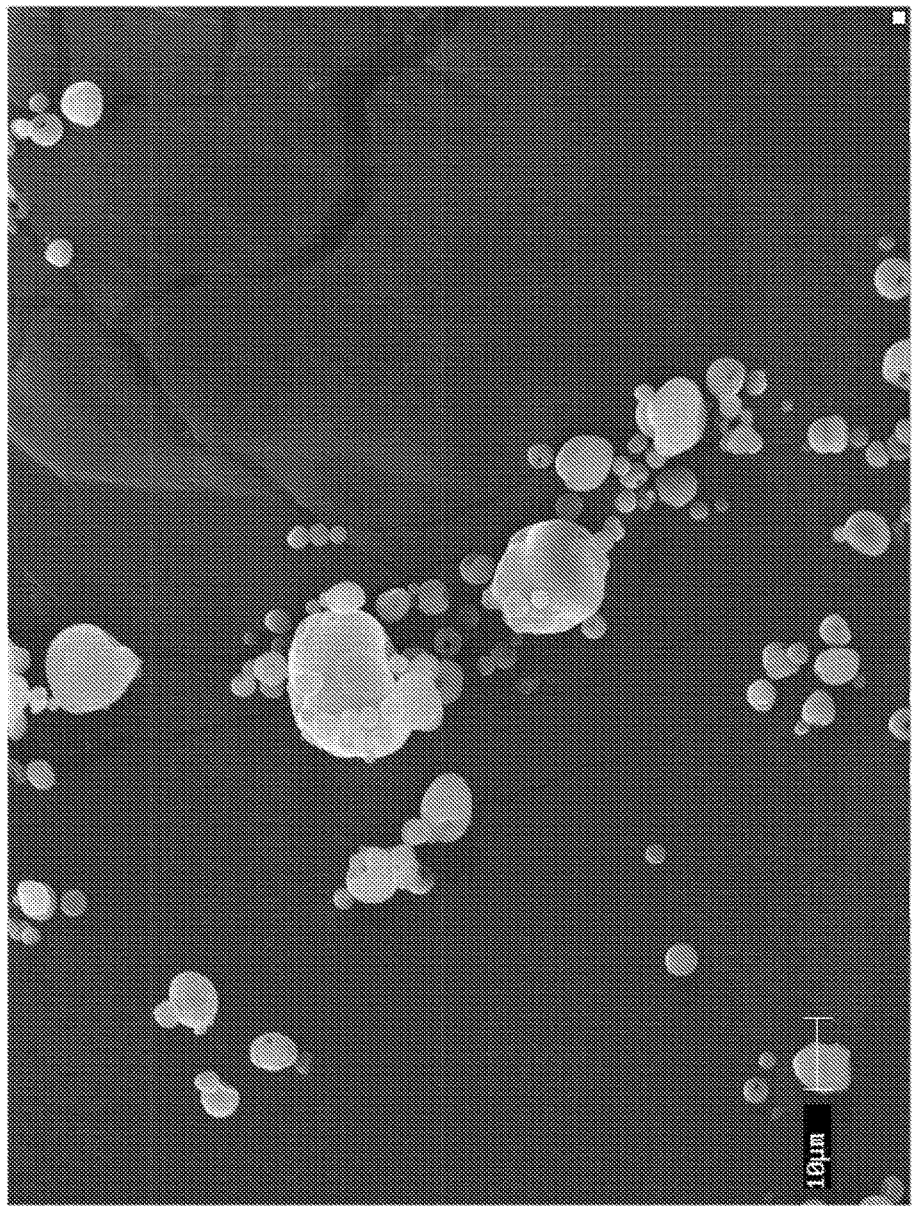
FIG. 6 is an SEM photo of non-thermal plasma deposited hydroxylapatite on a tooth substitute substrate.

FIG. 6 shows an SEM photo that shows the hydroxylapatite restoration material deposited on and affixed to a Tagua surface, which is known to have similar properties to a human tooth. (See U.S. 2013/0224684, which is incorporated herein by reference for all purposes.)

Example 2

Figure 7:
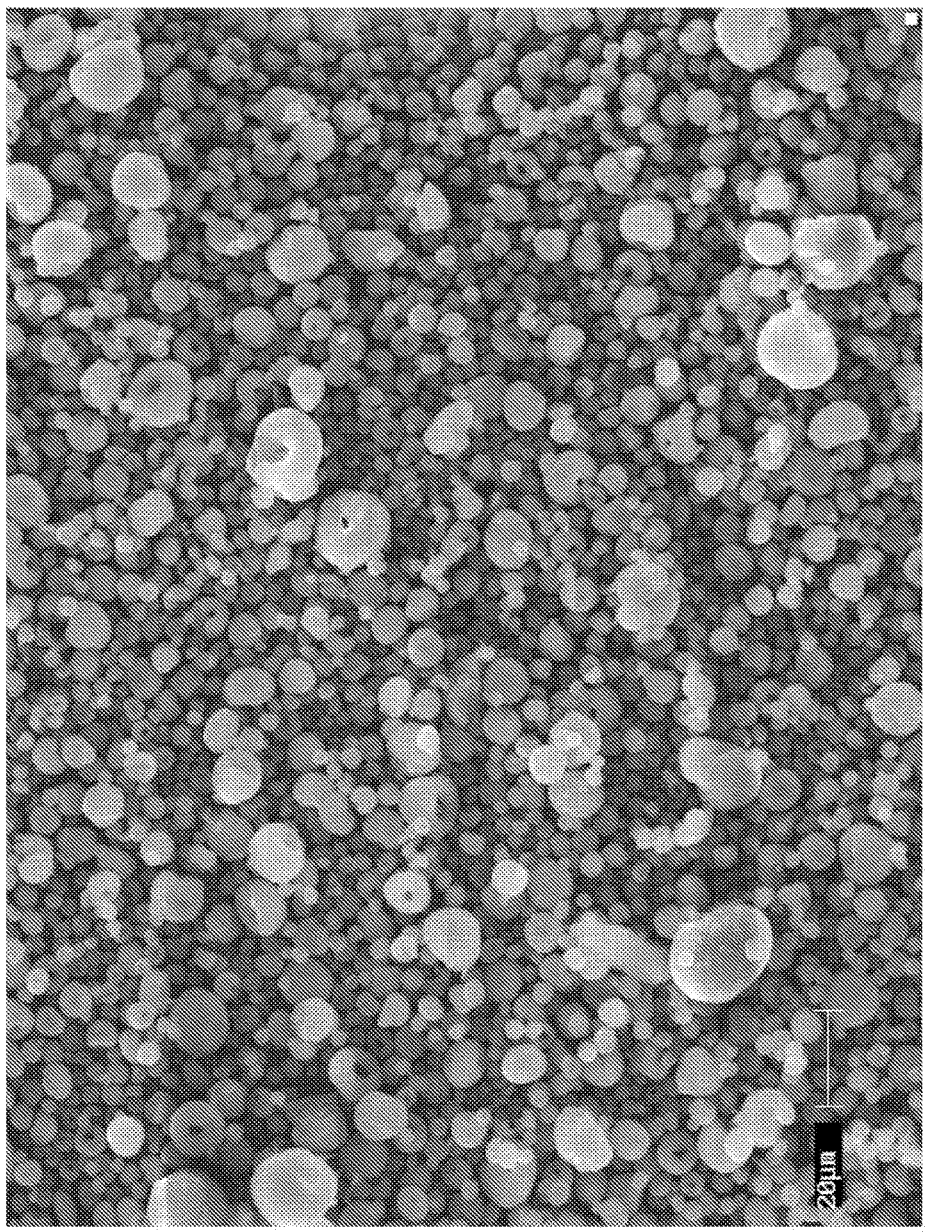
FIG. 7 is an SEM photo of several layers of non-thermal plasma deposited hydroxylapatite.

FIG. 7 is an SEM photo showing the hydroxylapatite crystals piling up in a significant thickness, such as would be useful to restore a damaged portion of tooth or bone by filling in a cracked, chipped, or otherwise damaged area.

Surprisingly, it was discovered that exciting the hydroxylapatite with a non-thermal plasma device produced new crystal growth in the deposited hydroxylapatite. This was observed in the figures as indicated by the angular crystalline features on the spherical particles and among them. This indicated new crystal growth and showed basic adhesion of the new crystals to old.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method for repairing a damaged bone or tooth, the method comprising:
    exciting a carrier gas to form an atmospheric plasma stream; and
    introducing a restoration material into the plasma stream to form a deposition stream; and depositing the restoration material on an application site by ejecting a plume of the deposition stream to the application site;
    wherein the restoration material comprises a mineral and the application site is the damaged bone or tooth.

2. The method of claim 1, further comprising depositing the restoration material until the damaged bone or tooth is restored.

3. The method of claim 1, wherein the restoration material is nanoscale hydroxyapatite or nano-scale diamond or combinations thereof.

4. The method of claim 3, wherein the restoration material is nano-scale hydroxyapatite.

5. The method of claim 1, wherein the application site is a dental cavity or damaged bone.

6. The method of claim 5, wherein the application site is a dental cavity.

7. The method of claim 5, wherein the application site is a damaged bone.

8. The method of claim 7, wherein the damaged bone is a degenerative disc or arthritic joint.

9. The method claim 1, wherein the plasma stream is non-thermal.

10. The method of claim 1, wherein a temperature, a pressure, and the gas of the method are selected and controlled such that no further damage occurs to the damaged bone or tooth and surrounding tissue.

11. The method of claim 1, wherein the carrier gas comprises helium.

12. A method for operating a handheld atmospheric plasma device including: a carrier gas source, a plasma needle, and a voltage source, and an additive mineral inlet; the method comprising:
producing a plasma stream;
the additive mineral inlet delivering a source of nanoscale mineral material to the plasma stream; and
depositing the plasma stream with nanoscale mineral material onto a damaged portion of a tooth or bone.

13. A method for repairing a damaged bone or tooth, the method comprising:
exciting a carrier gas to form an atmospheric plasma stream; and
depositing a restoration material onto an application site; and then
directing a plasma stream onto the restoration material on the application site;
wherein the application site is a damaged area of a tooth or bone;
wherein the restoration material comprises a nano-scale mineral.

14. The method of claim 13, further comprising crystallizing the restoration material when the plasma stream is directed onto the restoration material on the application site.

15. The method of claim 13, further comprising vacuuming residue from the application site.

16. The method of claim 13, wherein the nano-scale material is in solution.

17. The method of claim 13, further comprising moving an exhaust hood or protective hood coaxially with a deposition nozzle.

18. The method of claim 13, wherein the restoration material that is deposited on the application site is deposited at a thickness of 0.001 mm to 35 mm.

19. The method of claim 13, further comprising applying a vacuum at the application site that is 0.99 atm to 0.01 atm.

20. The method of claim 19, wherein the vacuum is further limited to a pressure that is less than a pressure that would disrupt the restoration material that is deposited onto the application site but is high enough to enhance the step of directing the plasma stream onto the restoration material on the application site.

* * * * *